US012766151B2

(12) United States Patent
Sawyer et al.

(10) Patent No.: US 12,766,151 B2
(45) Date of Patent: Oct. 20, 2026

(54) TESTOSTERONE COMPOSITIONS

(71) Applicant: Glia, LLC, Boston, MA (US)

(72) Inventors: Kenneth I. Sawyer, Boston, MA (US); Wei-Wei Chang, Boston, MA (US)

(73) Assignee: GLIA, LLC, Boston, MA (US)

( * ) Notice: Subject to any disclaimer, the term of this patent is extended or adjusted under 35 U.S.C. 154(b) by 1085 days.

(21) Appl. No.: 17/776,491

(22) PCT Filed: Nov. 13, 2020

(86) PCT No.: PCT/US2020/060373

§ 371 (c)(1),
(2) Date: May 12, 2022

(87) PCT Pub. No.: WO2021/097182

PCT Pub. Date: May 20, 2021

(65) Prior Publication Data

US 2022/0401458 A1 Dec. 22, 2022

Related U.S. Application Data

(60) Provisional application No. 62/934,661, filed on Nov. 13, 2019.

(51) Int. Cl.

| | |
|---|---|
| ***A61K 31/568*** | (2006.01) |
| ***A61K 9/00*** | (2006.01) |
| ***A61K 31/59*** | (2006.01) |
| ***A61P 25/16*** | (2006.01) |

(52) U.S. Cl.

CPC .......... *A61K 31/568* (2013.01); *A61K 9/0014* (2013.01); *A61K 31/59* (2013.01); *A61P 25/16* (2018.01)

(58) Field of Classification Search

CPC ................................ A61K 31/568; A61P 5/26
See application file for complete search history.

(56) References Cited

U.S. PATENT DOCUMENTS

| | | | | |
|---|---|---|---|---|
| 2006/0280783 | A1 | 12/2006 | Dipietro et al. | |
| 2008/0132475 | A1 | 6/2008 | Connor et al. | |
| 2009/0123571 | A1 | 5/2009 | Meehan | |
| 2013/0040922 | A1 | 2/2013 | Kreppner | |
| 2015/0031656 | A1 | 1/2015 | Podolski et al. | |
| 2016/0051565 | A1 * | 2/2016 | Wang .................. | A61K 31/366 514/171 |
| 2016/0250228 | A1 | 9/2016 | Kreppner et al. | |
| 2018/0064728 | A1 * | 3/2018 | Chang ..................... | A61P 25/08 |

FOREIGN PATENT DOCUMENTS

| | | | |
|---|---|---|---|
| BR | PI0611134 | A2 | 8/2010 |
| TW | 201811333 | A | 4/2018 |
| WO | 2006104726 | A2 | 5/2006 |
| WO | 2008070728 | A2 | 6/2008 |

OTHER PUBLICATIONS

International Search Report and Written Opinion for Application No. PCT/US2020/060373 mailed on Feb. 5, 2021, 11 pages.
Holland et al: "Differential response of sebaceous glands to exogenous testosterone", British Journal of Dermatology. vol. 139, No. 1,Jan. 4, 2002 (Jan. 4, 2002), pp. 102-103.
Rogol A D et al: "Natesto(TM), a novel testosterone nasal gel, normalizes androgen levels in hypogonadal men", Andrology, Scriptor Publisher Aps. vol. 4, No. 1,Dec. 22, 2015 (Dec. 22, 2015), pp. 46-54.
Shifren, et al., "Transdermal testosterone treatment in women with impaired sexual function after oophorectomy," Clinical Trial, N Engl J.Med., 343(10):682-8 (2000).

* cited by examiner

*Primary Examiner* — Sahar Javanmard

(74) *Attorney, Agent, or Firm* — Morse, Barnes-Brown & Pendleton, P.C.; Russell L. Widom; Erin E. Bryan, Esq.

(57) ABSTRACT

The present disclosure describes a method for treating a disease or condition selected from Parkinson's disease, traumatic brain injury, concussion, chronic traumatic encephalopathy, spinal cord injury, Sjögren's syndrome, Hashimoto's disease, lupus, psoriasis, psoriatic arthritis, rheumatoid arthritis, graft vs. host disease, hypogonadism, male metabolic syndrome, menopausal hormone insufficiency, and ocular surface disease, the method comprising topical administration of a testosterone composition to the forehead.

4 Claims, 3 Drawing Sheets

TESTOSTERONE COMPOSITIONS

CROSS-REFERENCES TO RELATED APPLICATIONS

This application claims priority to U.S. Provisional Patent Application Ser. No. 62/934,661 filed Nov. 13, 2019, which is incorporated by reference herein in its entirety.

BACKGROUND

Transdermal methods allow for the delivery of medicine directly through the skin. Gels, emulsions, creams, sprays and patches are easy to use and are effective for transdermal delivery of a drug. However, current transdermal delivery routes are utilized for delivering a drug either to exert a local effect or to enter the blood circulation.

Pharmaceuticals administered by all of the routes described above enter the bloodstream. Additionally, drugs in the circulation cannot always reach all areas of the body. For example, many drugs cannot pass through the blood-brain barrier. It also can be difficult to deliver a drug to an area of the body that is not well vascularized.

Topical testosterone gels are available commercially for use in hormone replacement therapy. However, the recommended daily dose of testosterone can be as high as 120 mg/day, which can lead to dose-dependent safety concerns.

The need exists for new routes of drug administration that allow for lower doses to be administered and that allow access of the drug to areas of the body which may be difficult to treat, such as the central nervous system.

BRIEF SUMMARY

Provided herein is a method for treating a symptom of a neurodegenerative condition. The method is carried out by topically administering a composition that contains testosterone to the forehead of the subject. The symptom treatable by the method is a motor symptom or a non-motor symptom of, for example, Parkinson's disease in a human subject in need thereof.

In some embodiments, a method is provided for treating traumatic brain injury, concussion, chronic traumatic encephalopathy, or spinal cord injury in a human subject in need thereof comprising, consisting of, or consisting essentially of topical administration of a testosterone composition to the forehead of the subject.

In some embodiments, a method is provided for treating Sjögren's syndrome, Hashimoto's disease, lupus, psoriasis, psoriatic arthritis, rheumatoid arthritis, or graft vs. host disease in a human subject in need thereof comprising, consisting of, or consisting essentially of topical administration of a testosterone composition to the forehead of the subject.

In some embodiments, a method is provided for treating hypogonadism in a human subject in need thereof comprising, consisting of, or consisting essentially of topical administration of a testosterone composition to the forehead of the subject.

In some embodiments, a method is provided for treating metabolic syndrome in a human male subject in need thereof comprising, consisting of, or consisting essentially of topical administration of a testosterone composition to the forehead of the subject.

In some embodiments, a method is provided for treating menopausal hormone insufficiency in a human subject in need thereof comprising, consisting of, or consisting essentially of topical administration of a testosterone composition to the forehead of the subject.

In some embodiments, a method is provided for treating an ocular surface disease in a human subject in need thereof comprising, consisting of, or consisting essentially of topical administration of a testosterone composition to the forehead of the subject.

DETAILED DESCRIPTION

I. General

Figure 1:
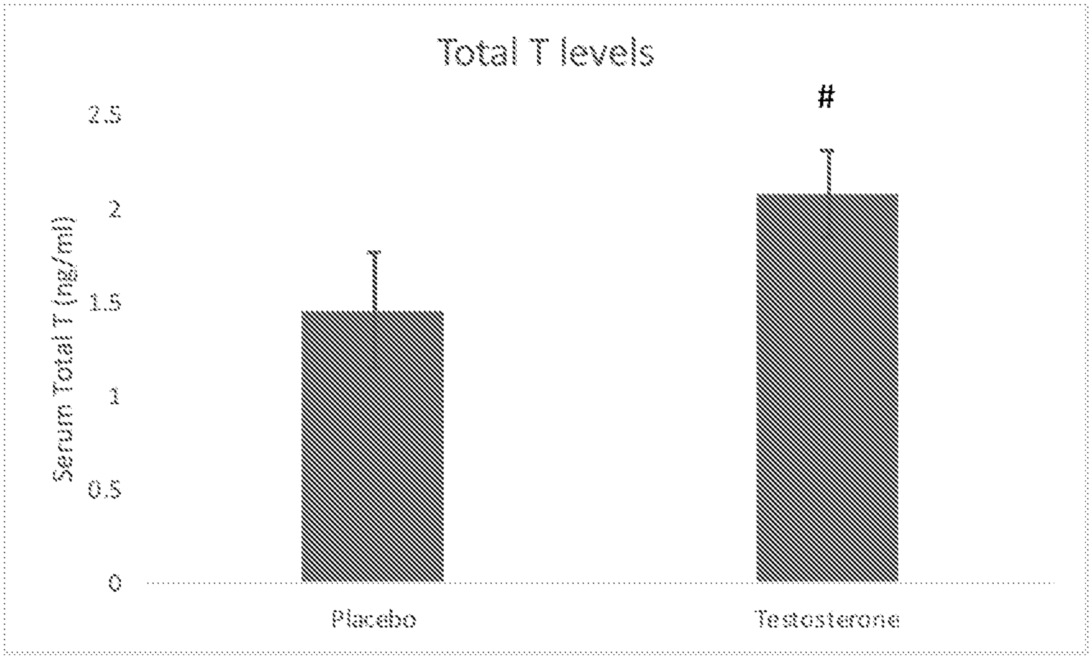
FIG. 1 shows the total serum testosterone levels (ng/mL) in a cohort of male Sprague-Dawley rats treated with a placebo composition (placebo) and a cohort treated with 0.2% testosterone (testosterone). The levels were measured after topical administration of a placebo or testosterone composition to the rat's shaved forehead twice daily over 14 days.

A cranial drug administration route is disclosed wherein testosterone is topically administered. This route of administration is believed to innervate cranial nerves, e.g., the trigeminal nerves, providing a complementary modality for treatment of diseases and conditions that cannot be treated easily via the vascular system. The topical composition can contain the active drug in concentrations from about 0.01% by weight to about 80% by weight. The testosterone can be formulated with appropriate excipients known in the art. The composition can be, e.g., a liquid or semi-solid, a solution, a suspension, an emulsion, a gel, a cream, a lotion, an ointment, or a patch. Administration can be simple or actively assisted by an electric current or other electrophysical device. The composition can be administered by applying it to the forehead.

Not to be bound by theory, it is believed that topical application of a compound, e.g., testosterone, to the forehead and/or temple areas can result in rapid action via a cranial nerve, such as cranial nerve V (trigeminal nerve), VII (facial nerve), I, II, III, IV, VI, VIII, IX, X, XI, and/or XII. It is also believed that the rapid action of drugs administered in such a way can be attributed to drug absorption of the drug through the skin of the forehead, including absorption via the transappendageal route through hair follicles and/or sebaceous glands on the skin, uptake by receptors residing in nerve endings in the skin, and induction of signaling in the brain. The brain or a region of the brain, such as the hypothalamus, can then respond to the drug by sending appropriate signals to target muscles, glands, and organs. For example, a drug that affects a cranial nerve can exert a therapeutic effect, e.g., by subsequent downstream signaling on the hypothalamus-pituitary-gonadal (HPG) or hypothalamus-pituitary-adrenal (HPA) axis, on an organ or gland that is innervated by that nerve. Another advantage of this drug administration route is evidenced by the observation that nerves damaged, extirpated, or infected by a virus, e.g., a neurotropic virus, can be treated by the method described above. Additionally, a lower dose of compound, as compared to the dose required for systemic delivery, can be effective, thereby enhancing safety.

II. Definitions

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

III. Compounds

The present disclosure is directed to topical compositions of testosterone (also known as 17β-hydroxyandrost-4-en-3-one, (8R,9S,10R,13S,14S,17S)-17-hydroxy-10,13-dimethyl-1,2,6,7,8,9,11,12,14,15,16,17-dodecahydrocyclopenta[α]phenanthren-3-one, and CAS ID: 58-22-0) having the following chemical structure:

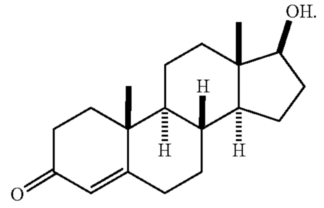

The present disclosure also contemplates topical compositions of a precursor of testosterone, including but not limited to androstenedione, dehydroepiandrosterone, and androstenediol.

In some embodiments, the topical testosterone composition is for use in treatment of Parkinson's disease in combination with calcitriol (also known as 1,25-dihydroxycholecalciferol, 1alpha,25-dihydroxyvitamin D3, 1,25-dihydroxyvitamin $D_3$, 1α,25-$(OH)_2D_3$, 1,25$(OH)_2D$, and CAS ID: 32222-06-3) having the following chemical structure:

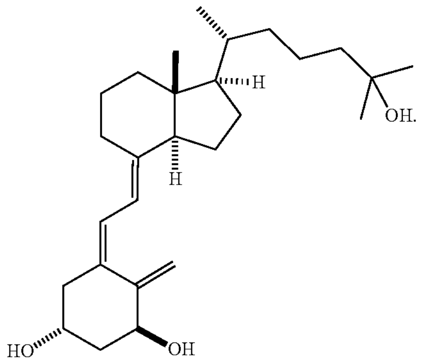 [SMILES: C=C1/C(=C\C=C2/CCC[C@]3(C)[C@@H]([C@H](C)CCCC(C)(C)O)CC[C@@H]23)C[C@@H](O)C[C@@H]1O]

IV. Compositions

In certain embodiments, the present disclosure provides a topical composition comprising testosterone and a pharmaceutically acceptable excipient.

In some embodiments, the composition is for use in the treatment of Parkinson's disease. In some embodiments, the composition further comprises calcitriol. In some embodiments, the composition comprises more testosterone than calcitriol. In some embodiments, the composition comprises at least 1.5, 2, 5, 10, 20, 30, 50, 100, 200, 300, 500, or 1000 times more testosterone than calcitriol.

In some embodiments, the composition is a liquid, a semi-solid, a solution, a suspension, an emulsion, a gel, a cream, a lotion, or an ointment.

In some embodiments, the composition is formulated for delivery in a patch.

In some embodiments, the composition is formulated for topical or subcutaneous delivery in an implant device.

In some embodiments, a topical composition comprises testosterone in concentrations from about 0.001% to about 20%, e.g., from about 0.001% to about 10%, from about 0.005% to about 10%, from about 0.01% to about 10%, from about 0.01% to about 5%, from about 0.01% to about 2.5%, from about 0.1% to about 5%, or from about 0.1% to about 2.5%, by weight. For example, the testosterone concentration can be 0.001%, 0.025%, 0.005%, 0.01%, 0.025%, 0.05%, 0.1%, 0.2%, 0.25%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 5%, 10%, or 20%, or any range defined by two numbers of the foregoing.

V. Administration

Testosterone may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the subject's life.

The dosage or dosing frequency of testosterone may be adjusted over the course of the treatment, based on the judgment of the administering physician.

The composition may be administered to a subject (e.g., a human subject) in an amount effective to produce the desired therapeutic effect. In certain embodiments, the composition is administered twice daily or once daily.

The testosterone composition can be administered topically to the face to the regions that are outside of the palpebral part of the eye. The palpebral part of the eye refers to the region of and around the eye associated with the palpebral component of the orbicularis oculi muscle group. The palpebral component of the muscles originates in the palpebral ligament and runs above and below the eye to the lateral angle of the eye, forming concentric circles around the eye. The palpebral part of the eye thus refers to the facial surface around the eye that corresponds to the location of the palpebral component of the orbicularis oculi muscle lying underneath the facial skin.

Non-limiting examples of facial regions for topical administration include, for example, the forehead above the eyebrows, the temple area between the end of the eyebrow and the hairline including the temple region, the upper cheek, or the sides or bridge of the nose. In some embodiments, the composition of the present invention is administered to the forehead. In some embodiments, the composition is administered to one or both temple regions. In some embodiments, the composition is administered to the upper cheek. In some embodiments, the composition is administered to one or both sides or the bridge of the nose. In some embodiments, the composition is administered to two or more regions of the face simultaneously or sequentially, and proximately or distant in time. For example, the composition can be administered to the forehead, and further administered to the temple region at the same time or at the next prescribed time, whether the next prescribed time is the same day or a different day. In some embodiments, the composition is administered to the same region of the face for each administration. In some embodiments, the composition is administered to any area of the skull, exclusive of the palpebral part of the eye.

In some embodiments, the amount of testosterone that is administered is from about 0.001 mg to about 20 mg, such as from 0.001 mg to 1 mg, from 0.001 mg to 0.8 mg, from 0.001 mg to 0.5 mg, from 0.001 mg to 0.25 mg, from 0.001 mg to 0.2 mg, from 0.01 mg to 1 mg, from 0.01 mg to 0.5 mg, or from 0.01 mg to 0.25 mg. For example, the amount of testosterone that is administered can be about 0.001, 0.005, 0.01, 0.025, 0.05, 0.1, 0.2, 0.25, 0.3, 0.4, 0.5, 0.6, 0.7, 0.8, 0.9, 1, 2, 2.5, 5, 10, 20 mg, or any range defined by two numbers of the foregoing.

In some embodiments, the testosterone is administered in conjunction with at least one additional therapeutic agent.

In some embodiments, the topical testosterone composition is administered for treatment of Parkinson's disease. In some embodiments, the testosterone is administered in conjunction with calcitriol. In some embodiments, the testosterone and the calcitriol is administered sequentially, i.e., the testosterone is administered before the calcitriol or the testosterone is administered after the administration of the calcitriol. In some embodiments, the testosterone is administered about 5, 10, 15, 20, 30, 45, 60 minutes or more after the calcitriol. In some embodiments, the calcitriol is administered about 5, 10, 15, 20, 30, 45, 60 minutes or more after the testosterone. In some embodiments, the testosterone and the calcitriol is administered simultaneously. In some embodiments, the administration comprises at least 1.5, 2, 5, 10, 20, 30, 50, 100, 200, 300, 500, or 1000 times more testosterone than calcitriol. In some embodiments, the amount of calcitriol that is administered is from about 0.05 to 50 μg calcitriol, such as from about 0.1 to 10, 0.1 to 20, 0.1 to 25, or from about 0.2 to 0.8 μg calcitriol. For example, the amount of calcitriol that is administered can be about 0.05, 0.1, 0.2, 0.3, 0.4, 0.5, 0.6, 0.7, 0.8, 0.9, 1, 1.5, 2, 2.5, 3, 4, 5, 10, 20, 30, 40, or about 50 μg, or any range defined by two numbers of the foregoing.

VI. Methods

The topical testosterone compositions described herein are generally useful in a method for treating a number of diseases or conditions, such as a neurodegenerative condition, an autoimmune disease, or a testosterone insufficiency, in a human subject in need thereof. In some embodiments, the human subject is male. In some embodiments, the human subject is female. In some embodiments, the human subject is adult. In some embodiments, the human subject is pediatric. In some embodiments, the method comprises, consists essentially of, or consists of administration of the composition to the forehead of the subject.

Neurodegenerative conditions that can be treated with a method described herein include traumatic brain injury, concussion, chronic traumatic encephalopathy (CTE), spinal cord injury, and Parkinson's disease.

In some embodiments, the method comprises treatment of traumatic brain injury in a human subject. Traumatic brain injury can result from a violent blow or jolt to the head or body. An object that penetrates brain tissue, such as a bullet or shattered piece of skull, also can cause a traumatic brain injury. Symptoms of a traumatic brain injury can be mild, moderate or severe, depending on the extent of damage to the brain. Mild cases may result in a brief change in mental state or consciousness, while severe cases may result in extended periods of unconsciousness, coma or even death.

In some embodiments, the method comprises treatment of concussion in a human subject. A concussion is a mild traumatic brain injury. It can occur after an impact to the head or after a whiplash-type injury that causes the head and brain to shake quickly back and forth. A concussion can result in an altered mental state that may include becoming unconscious.

In some embodiments, the method comprises treatment of chronic traumatic encephalopathy (CTE) in a human subject. Chronic traumatic encephalopathy (CTE) is a neurodegenerative disease caused by repeated head injuries. Symptoms may include behavioral problems, mood problems, and problems with thinking Symptoms often do not begin until years after the injuries. CTE may get worse over time and can result in dementia.

In some embodiments, the method comprises treatment of a spinal cord injury in a human subject. A spinal cord injury is damage to the spinal cord that results in a loss of function, such as mobility and/or feeling. Frequent causes of spinal cord injuries are trauma, e.g., car accident, gunshot, falls, etc., or disease, e.g., polio, spina bifida, Friedreich's ataxia, etc.

In some embodiments, the method comprises treatment of Parkinson's disease in a human subject. Parkinson's disease is a progressive and chronic neurodegenerative brain disorder. For the treatment of Parkinson's disease, the method comprises administration of a topical testosterone composition, optionally in conjunction with a calcitriol composition. In some embodiments, the testosterone composition further comprises calcitriol. In some embodiments, the method comprises, consists essentially of, or consists of administration to the forehead of the subject. The presence of at least two of the following motor symptoms provides a presumptive diagnosis: resting tremor, bradykinesia (slowed movement), rigidity (dystonia), and postural instability. Other motor and physiological symptoms include kinetic tremor, uncontrolled movement (dyskinesia), restless leg, freezing, impaired balance and coordination, constipation, urinary incontinence and urgency, swallowing difficulty, olfactory dysfunction, weight loss, hypertension, shortness of breath, pain, excessive sweating, cramping and muscle aches, and fatigue. In some embodiments, the Parkinson's disease comprises hypogonadism. Cognitive symptoms may include cognitive impairment, anorexia, mood disorders, sleep disturbances, speech difficulties, handwriting problems, visual disturbances, a memory deficit, e.g., loss of short term or long term memory, impaired comprehension, apathy, impulsivity, depression, and anxiety. Carbidopa-levodopa remains the standard of treatment for the symptoms of Parkinson's disease. Side effects with carbidopa-levodopa may include severe dyskinesia and other symptoms similar to the disease being treated.

Autoimmune diseases that can be treated with a method described herein include Sjögren's syndrome, Hashimoto's disease, lupus, psoriasis, psoriatic arthritis, rheumatoid arthritis, and graft vs. host disease (e.g., chronic graft vs. host disease or acute graft vs. host disease).

In some embodiments, the method comprises treatment of Sjögren's syndrome in a human subject. Sjögren's syndrome is a disorder of your immune system identified by its two most common symptoms: dry eyes and a dry mouth. The condition often accompanies other immune system disorders, such as rheumatoid arthritis and lupus. In Sjögren's syndrome, the mucous membranes and moisture-secreting glands of your eyes and mouth are usually affected first, resulting in decreased tears and saliva.

In some embodiments, the method comprises treatment of Hashimoto's disease in a human subject. Hashimoto's disease is a condition in which your immune system attacks the thyroid. Inflammation from Hashimoto's disease, also known as chronic lymphocytic thyroiditis, often leads to an underactive thyroid gland (hypothyroidism). Hashimoto's disease is the most common cause of hypothyroidism. It primarily affects middle-aged women but can also occur in men and women of any age and in children.

In some embodiments, the method comprises treatment of lupus in a human subject. Lupus, also known as systemic lupus erythematosus, is a systemic autoimmune disease. Inflammation caused by lupus can affect many different body systems, including joints, skin, kidneys, blood cells, brain, heart and lungs. The signs and symptoms of lupus depends on which body systems are affected by the disease. The most common signs and symptoms include: fatigue; fever; joint pain, stiffness and swelling; butterfly-shaped rash on the face that covers the cheeks and bridge of the nose or rashes elsewhere on the body; skin lesions that appear or worsen with sun exposure (photosensitivity); fingers and toes that turn white or blue when exposed to cold or during stressful periods (Raynaud's phenomenon); shortness of breath; chest pain; dry eyes; and/or headaches, confusion and memory loss.

In some embodiments, the method comprises treatment of psoriasis in a human subject. Psoriasis is a skin condition that speeds up the life cycle of skin cells. It causes cells to build up rapidly on the surface of the skin. The extra skin cells form scales and red patches that are itchy and sometimes painful. Psoriasis is a chronic disease that may have flare and remission stages.

In some embodiments, the method comprises treatment of psoriatic arthritis in a human subject. Psoriatic arthritis is a form of arthritis that affects some people who have psoriasis, a condition that features red patches of skin topped with silvery scales. Most people develop psoriasis first and are later diagnosed with psoriatic arthritis, but the joint problems can sometimes begin before skin patches appear. Joint pain, stiffness and swelling are the main signs and symptoms of psoriatic arthritis. They can affect any part of the body, including fingertips and spine, and can range from relatively mild to severe. In both psoriasis and psoriatic arthritis, disease flares may alternate with periods of remission.

In some embodiments, the method comprises treatment of rheumatoid arthritis in a human subject. Rheumatoid arthritis is a chronic inflammatory disorder that affects the lining of the joints, causing a painful swelling that can eventually result in bone erosion and joint deformity. In some people, the condition can also damage a wide variety of body systems, including the skin, eyes, lungs, heart and blood vessels.

In some embodiments, the method comprises treatment of graft vs. host disease in a human subject. In some embodiments, the disease is chronic. In some embodiments, the disease is acute. Graft-versus-host disease (GVHD) is an immune condition that occurs after transplant procedures when immune cells from the donor (known as the graft or graft cells) attack the recipient patient host's tissues. The chronic disease may occur after an allogeneic bone marrow transplant (stem cell transplant).

In some embodiments, the method comprises treatment of hypogonadism in a human subject. The human subject may be adult or pediatric. Hypogonadism occurs when the sex glands or gonads produce little or no sex hormones. The gonads are primarily the testes in males and the ovaries in females. Thus, primary hypogonadism can occur with damage or removal of the gonads. Central (or secondary) hypogonadism occurs when the brain does not signal to the gonads to produce a sufficient level of sex hormones. Symptoms of hypogonadism in females may include: lack of menstruation, slow or absent breast growth, hot flashes, loss of body hair, low or absent sex drive, and milky discharge from breasts. Symptoms of hypogonadism in males may include: loss of body hair, muscle loss, abnormal breast growth, reduced growth of penis and testicles, erectile dysfunction, osteoporosis, low or absent sex drive, infertility, fatigue, hot flashes, and difficulty concentrating. Hypogonadism may be a symptom of other diseases. For example, pediatric male hypogonadism may occur due to Klinefelter syndrome, which results from two or more X chromosomes.

In some embodiments, the method comprises treatment of metabolic syndrome in a human male subject. Metabolic syndrome is a multi-system disorder marked by combinations of glucose intolerance, obesity, hypertension, and dyslipidemia. Male metabolic syndrome can comprise hypogonadism.

In some embodiments, the method comprises treatment of menopausal hormone insufficiency in a human subject. Menopausal hormone insufficiency can be a result of menopause, perimenopause, or primary ovarian insufficiency. Primary ovarian insufficiency, also known as premature ovarian failure, happens when a woman's ovaries stop working normally before age 40. In some embodiments, the method comprises, consists essentially of, or consists of administration to the forehead of the subject.

In some embodiments, the method comprises treatment of an ocular surface disease in a human subject. Ocular surface diseases include conditions such as Dry Eye Disease (DED), blepharitis and meibomian gland dysfunction (MDG), allergic eye diseases (AED), chemical and thermal burns and so on. Ocular surface diseases can severely affect eyesight and quality of life, and in severe cases, cause blindness. In some embodiments, the method comprises, consists essentially of, or consists of administration to the forehead of the subject.

Further provided herein is a topical testosterone composition for use in treating a disease or condition in a human subject selected from the group consisting of Parkinson's disease, traumatic brain injury, concussion, chronic traumatic encephalopathy, spinal cord injury, Sjögren's syndrome, Hashimoto's disease, lupus, psoriasis, psoriatic arthritis, rheumatoid arthritis, graft vs. host disease, hypogonadism, male metabolic syndrome, menopausal hormone insufficiency, and ocular surface disease. In some embodiments, the disease or condition is Parkinson's disease. In some embodiments, the disease or condition is Parkinson's disease. In some embodiments, the disease or condition is traumatic brain injury. In some embodiments, the disease or condition is concussion. In some embodiments, the disease or condition is chronic traumatic encephalopathy. In some embodiments, the disease or condition is spinal cord injury. In some embodiments, the disease or condition is Sjögren's syndrome. In some embodiments, the disease or condition is Hashimoto's disease. In some embodiments, the disease or condition is lupus. In some embodiments, the disease or condition is psoriasis. In some embodiments, the disease or condition is psoriatic arthritis. In some embodiments, the disease or condition is rheumatoid arthritis. In some embodiments, the disease or condition is graft vs. host disease. In some embodiments, the disease or condition is hypogonadism. In some embodiments, the disease or condition is male metabolic syndrome. In some embodiments, the disease or condition is menopausal hormone insufficiency. In some embodiments, the disease or condition is ocular surface disease. In some embodiments, the use comprises, consists essentially of, or consists of administration to the forehead of the subject.

Further provided herein is the use of a topical testosterone composition in treating a disease or condition selected from the group consisting of Parkinson's disease, traumatic brain injury, concussion, chronic traumatic encephalopathy, spinal cord injury, Sjögren's syndrome, Hashimoto's disease, lupus, psoriasis, psoriatic arthritis, rheumatoid arthritis, graft vs. host disease, hypogonadism, male metabolic syndrome, menopausal hormone insufficiency, and ocular surface disease in a human subject. In some embodiments, the disease or condition is Parkinson's disease. In some embodiments, the disease or condition is traumatic brain injury. In some embodiments, the disease or condition is concussion. In some embodiments, the disease or condition is chronic traumatic encephalopathy. In some embodiments, the disease or condition is spinal cord injury. In some embodiments, the disease or condition is Sjögren's syndrome. In some embodiments, the disease or condition is Hashimoto's disease. In some embodiments, the disease or condition is lupus. In some embodiments, the disease or condition is psoriasis. In some embodiments, the disease or condition is psoriatic arthritis. In some embodiments, the disease or condition is rheumatoid arthritis. In some embodiments, the disease or condition is graft vs. host disease. In some embodiments, the disease or condition is hypogonadism. In some embodiments, the disease or condition is male metabolic syndrome. In some embodiments, the disease or condition is menopausal hormone insufficiency. In some embodiments, the disease or condition is ocular surface disease. In some embodiments, the use comprises, consists essentially of, or consists of administration to the forehead of the subject.

Also provided herein is the use of a testosterone in the manufacture of a topical medicament for administration to a human subject in treating a disease or condition selected from the group consisting of Parkinson's disease, traumatic brain injury, concussion, chronic traumatic encephalopathy, spinal cord injury, Sjögren's syndrome, Hashimoto's disease, lupus, psoriasis, psoriatic arthritis, rheumatoid arthritis, graft vs. host disease, hypogonadism, male metabolic syndrome, menopausal hormone insufficiency, and ocular surface disease. In some embodiments, the disease or condition is Parkinson's disease. In some embodiments, the disease or condition is traumatic brain injury. In some embodiments, the disease or condition is concussion. In some embodiments, the disease or condition is chronic traumatic encephalopathy. In some embodiments, the disease or condition is spinal cord injury. In some embodiments, the disease or condition is Sjögren's syndrome. In some embodiments, the disease or condition is Hashimoto's disease. In some embodiments, the disease or condition is lupus. In some embodiments, the disease or condition is psoriasis. In some embodiments, the disease or condition is psoriatic arthritis. In some embodiments, the disease or condition is rheumatoid arthritis. In some embodiments, the disease or condition is graft vs. host disease. In some embodiments, the disease or condition is hypogonadism. In some embodiments, the disease or condition is male metabolic syndrome. In some embodiments, the disease or condition is menopausal hormone insufficiency. In some embodiments, the disease or condition is ocular surface disease. In some embodiments, the use comprises, consists essentially of, or consists of administration to the forehead of the subject.

In some embodiments, the subject has one or more of the aforementioned diseases or conditions.

VII. Examples

Example 1

Testosterone Administration to Rat Forehead

An animal model using adult male Sprague-Dawley rats (10 treated, 10 placebo) was used to determine the effect of twice daily topical administration of testosterone to the forehead. Each animal was shaved from the periorbital region to the apex of the skull under isoflurane anesthesia. Shaving was conducted 1 day prior to drug application and prior to drug administration on day 8. The gel was applied to the shaved region at 10 am and 2 pm each day for 14 days. Thirty minutes following the final application, the rats were overdosed with pentobarbital prior to collection of cardiac blood and brain tissue. The concentration was about 0.2% testosterone delivered with a metered dose.

Hormone Assessment: Blood was collected, stored at 4° C. overnight and spun down to collect serum. Serum was analyzed for total testosterone levels (T) and luteinizing hormone (LH) levels by competitive ELISA using commercially available kits (Enzo Life Sciences). For assessing testosterone levels, serum was diluted 1:20 and treated with a steroid displacement reagent to allow assessment of total testosterone levels. All samples were run in duplicate. For assessing LH, serum was diluted 1:2 and, due to high variance, samples were run in quadruplet. Obvious outlying values were omitted and data were averaged for the final analysis.

Brain Activation: Brains were collected, fixed in 4% PFA via intra-cardiac perfusion and 24 hours of post-fixing. Tissue was then stored in 30% sucrose at 4° C. for 72 hours for cryoprotection. Four to eight 15 uM sections were collected near plates 18 and 21 of the Paxinos and Watson adult rat brain atlas. The best sections were then processed using RNA SCOPE technology to perform florescent in situ hybridization using probes targeting GnRH and c-FOS mRNA. About 200 images per brain section were captured at 20× using a Keyence microscope. Individual sections were then stitched together using commercial software. Levels of fluorescence were examined in the Medial Preoptic region of the Hypothalamus using FIJI (Image-J) software following a Renyi thresholding procedure. There were four measures considered, the area of the region showing positive staining, the average brightness of the positive staining, a hybrid measure (termed density) which was calculated by multiplying the area by brightness, and the number of districting positively stained objects.

A 42% increase in testosterone levels in the treated rats was observed when compared to controls (FIG. 1). Based on strong directional hypothesis that testosterone would increase in the treated subject, a one-way t-test was performed and yielded a p value of 0.08. A slight increase (9%) in serum luteinizing hormone levels was observed in the testosterone-treated subjects, which was not statistically significant. There were no significant effects of testosterone treatment on c-Fos expression in the anterior or the posterior medial preoptic region of the hypothalamus.

Figure 2:
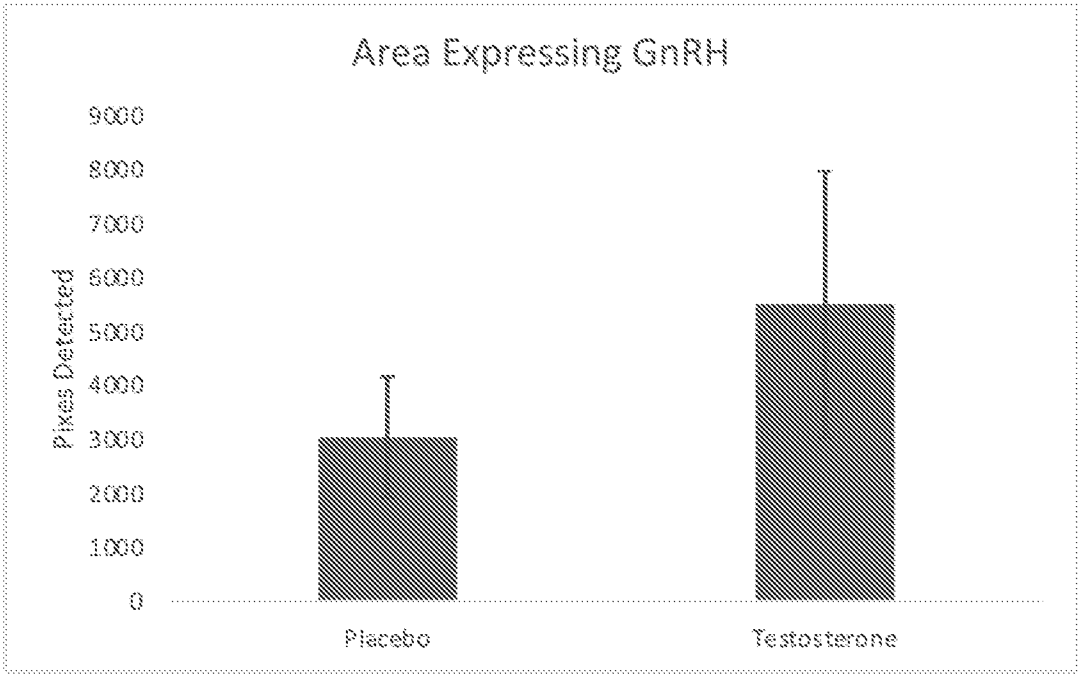
FIG. 2 shows the gonadotropin-releasing hormone (GnRH) expression as a function of area expressing GnRH in the anterior medial preoptic region of the hypothalamus in rats treated with placebo or testosterone according to Example 1.
Figure 3:
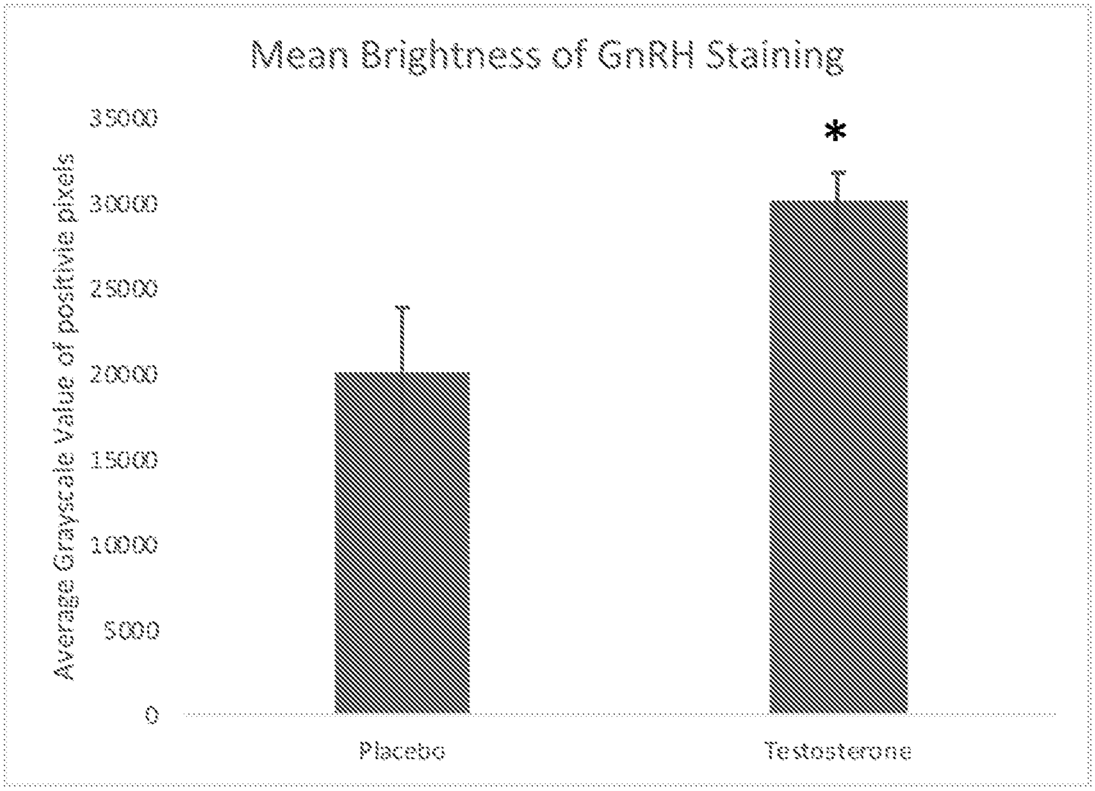
FIG. 3 shows the gonadotropin-releasing hormone (GnRH) expression as a function of mean brightness of GnRH staining in the anterior medial preoptic region of the hypothalamus in rats treated with placebo or testosterone according to Example 1.
Figure 4:
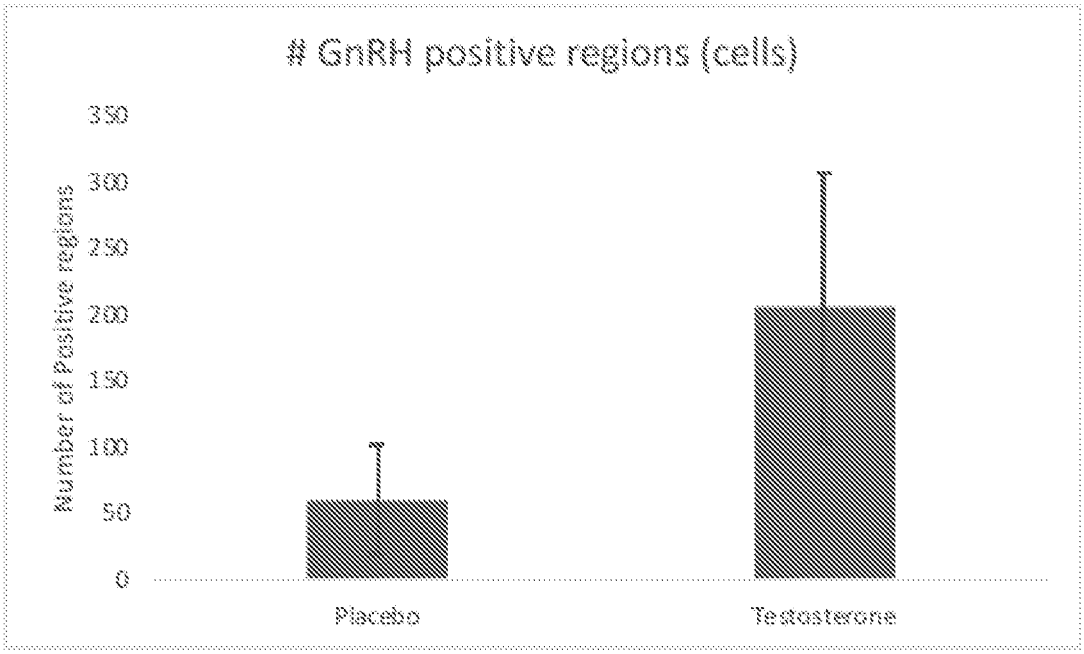
FIG. 4 shows the gonadotropin-releasing hormone (GnRH) expression as a function of number of GnRH positive cell regions in the anterior medial preoptic region of the hypothalamus in rats treated with placebo or testosterone according to Example 1.

Rats receiving the testosterone application showed an increase in GnRH expression in the anterior medial preoptic region of the hypothalamus (FIG. 2). This was observed numerically in all measures, but only reached statistical significance in the average brightness measure ($p<0.05$) (FIG. 3). Although the number of GnRH positive regions does not reach significance, there is little overlap between the populations (FIG. 4). Overall, these data suggested that forehead application of testosterone enhanced GnRH expression in existing GnRH+ cells.

There was much lower GnRH expression in the posterior medial preoptic region of the hypothalamus and no differences due to testosterone treatment in area expressing GnRH, mean brightness of GnRH staining, overall density of GnRH staining, or the number of GnRH positive regions.

Example 2

Topical Testosterone Effect on Corneal Mechanical Threshold in Rat

Figure 5:
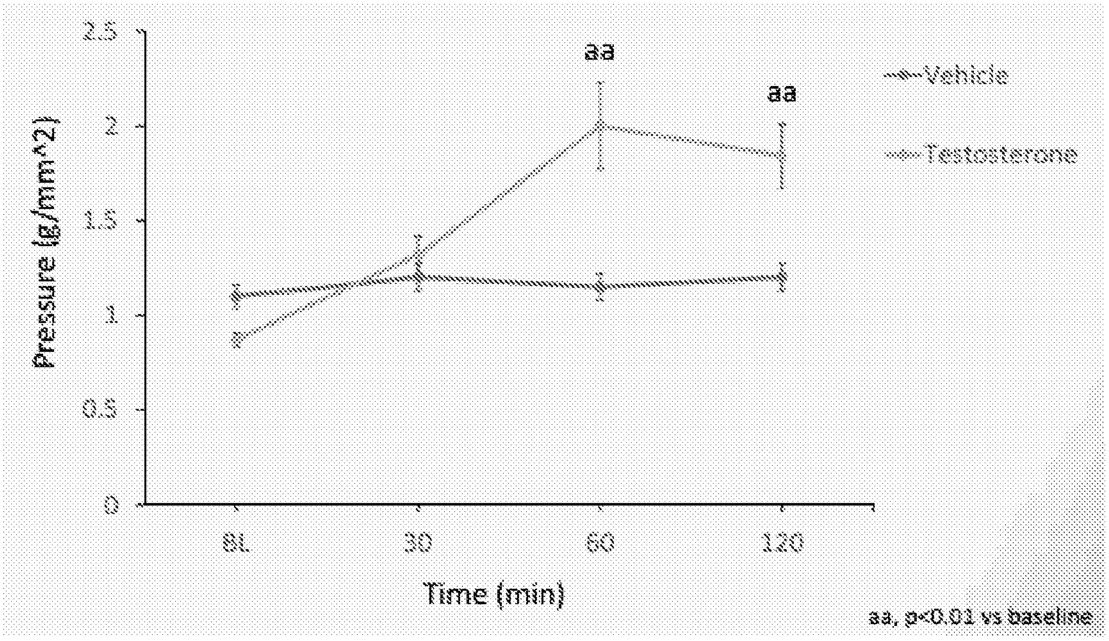
FIG. 5 shows pressure (g/$mm^2$) vs. time (min) in a measurement of corneal mechanical thresholds before (BL) or after topical administration of vehicle or a testosterone composition to the head of a rat.

In the same animal model as used in Example 1, the corneal mechanical thresholds were determined as a surrogate for effect on dry eye. The corneal mechanical thresholds measured in pressure (g/mm$^2$) were determined before administration (BL), or after administration of a control (vehicle) composition or testosterone composition to the shaved head of the rat. FIG. 5 shows that the pressure was significantly higher ($p<0.01$) in the testosterone treated animals 60 or 120 minutes after administration compared with control.

Example 3

Case Study: Patient SL—Female, 78 Years of Age

In 2008, patient had a total hysterectomy with ovaries removed. She was diagnosed with Parkinson's in May 2016, confirmed October 2016 and April 2017 by independent DAT scans. Symptoms were bradykinesia of the legs, rigidity/stiffness, postural instability, specifically trouble with balance and falling as well as trouble with moving and walking, with peripheral neuropathy on both feet. Patient experienced no particular tremors. She also experienced chronic and increasing fatigue and loss of energy, as well as chronic head colds that would last about one week at a time every 6 weeks.

Co-morbidity: patient was diagnosed with bipolar disorder in 2016.

In February 2019, symptoms continued and progressed. Patient was prescribed carbidopa/levodopa 25 mg/100 mg TID. Patient legs and arms were feeling weak, with the legs worse than the arms, reporting "it is hard for me to get up and down from the ground, to get in and out of a swimming pool and so forth." Patient was instructed to apply testosterone dose of 0.14 mg in 0.07 g topical gel in a once daily application to forehead. Patient started on testosterone topical gel due to symptom progression, reporting prior to initial dose she had low energy and had a cold for 3 days. After starting the testosterone gel, patient started to feel more energetic and was able to exercise.

Two months later, physician reported patient's total testosterone of 14 ng/dL and free testosterone is 0.08 pg/mL, identical to February values prior to initiating topical testosterone treatment. After ten months treatment, patient reported total testosterone of 21 ng/dL and free testosterone 1.0 pg/mL, with bioavailable testosterone 2.0 ng/dL. Patient was maintained at these levels. The below Table summarizes these results.

TABLE

| Post-treatment with topical testosterone (0.2% w/w) | Free testosterone (pg/mL) | Total testosterone (ng/dL) |
|---|---|---|
| 0 months | 0.08 | 14 |
| 2 months | 0.08 | 14 |
| 10 months | 1.0 | 21 |

Covering the 20-month period patient was on testosterone topical gel applied to the forehead: patient stated that her physical trainer reported "Much better compared to 6 and 12 months ago. Stronger—similar, heavier weights and more quickly. Had been having more trouble with legs earlier and recently hasn't had as much trouble with knees. Increased repetitions about 25% in exercises." Patient stated "I've gotten better rather than worse. My walking has not gotten worse, it's about the same. My knees were better than they were a year ago."

In April 2020, patient decreased carbidopa/levodopa dosing from three times daily to once per day and also discontinued exogenous supplemental estradiol. Patient still had no tremors, but did exhibit increased strength in knees and rest of body, and was energetic as her neurologist was impressed by her workout routine compared to other Parkinson's patients. Patient SL showed no cognitive decline, and had increased sex drive compared to before start of testosterone treatment.

In June 2020, neurologist concluded that Patient SL's Parkinson's disease had not progressed and was impressed with the exercise patient SL was doing. The neurologist thought she was doing great and advised there was no need for patient to move into assisted living facility. Patient also reported increased sex drive over the last year as compared to years before. In verbal communication, patient was an attentive communicator, upbeat in affect, cognitively present and highly responsive in conversation, able to recall facts, dates, names, locations and appointments without hesitation in the past.

Patient belonged to a Parkinson's peer group since being diagnosed in 2017. There were 30 people in the peer group. Two of the 30 patients have died from Parkinson's related disease, 100%, with the exception of Patient SL, have progressed in disease. Around 20-25% of the peer group have progressed with major cognitive problems including dementia. 20% of the peer group have become wheelchair bound. While Parkinsonian peers, male and female, had disease progression effecting onset of dementia, cognitive decline, emotional problems and motor symptoms, Patient SL had not progressed in any of these aspects of the disease.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for treating hypogonadism in a human subject, the method comprising topical administration of a testosterone composition to the forehead of the human subject, wherein testosterone is the only therapeutic agent administered in the method and 0.01 mg to 0.5 mg testosterone is administered daily.

2. The method of claim 1 comprising twice daily or once daily administration.

3. The method of claim 1, wherein the human subject is adult.

4. The method of claim 1, wherein the human subject is pediatric.

* * * * *